(12) United States Patent
Heinrich et al.

(10) Patent No.: US 7,834,032 B2
(45) Date of Patent: Nov. 16, 2010

(54) PIPERIDINE DERIVATIVES

(75) Inventors: Timo Heinrich, Gross-Umstadt (DE); Henning Boettcher, Darmstadt (DE); Joachim Leibrock, Pfungstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 1073 days.

(21) Appl. No.: 10/590,912

(22) PCT Filed: Feb. 14, 2005

(86) PCT No.: PCT/EP2005/001446

§ 371 (c)(1), (2), (4) Date: Aug. 28, 2006

(87) PCT Pub. No.: WO2005/082886

PCT Pub. Date: Sep. 9, 2005

(65) Prior Publication Data

US 2007/0197596 A1    Aug. 23, 2007

(30) Foreign Application Priority Data

Feb. 27, 2004   (DE) .................. 10 2004 010 132

(51) Int. Cl.
*A61K 31/454* (2006.01)
*C07D 401/02* (2006.01)

(52) U.S. Cl. ...................... 514/323; 546/201
(58) Field of Classification Search .............. 514/323; 546/201
See application file for complete search history.

(56) References Cited

U.S. PATENT DOCUMENTS 6,815,456 B2 * 11/2004 Zhou et al. ................. 514/322

FOREIGN PATENT DOCUMENTS

| EP | 0208235 A | 1/1987 |
|---|---|---|
| EP | 0319962 A | 6/1989 |
| EP | 0320983 A | 6/1989 |
| EP | 0337136 A | 10/1989 |
| WO | WO 95/24194 A | 9/1995 |
| WO | WO 99/11641 A | 3/1999 |
| WO | WO 99/46245 A | 9/1999 |
| WO | WO 02/44168 A | 6/2002 |

OTHER PUBLICATIONS

Suddon "Pseudopolymorph . . . " Crystal growth & design 4(6) p. 1087 (2004) (two page from internet).*
Brga et al. "making crystals . . . " Chem. Commun. p. 3635-3645 (2005).*
Kim et al. "new serotonin 5HT6 . . . " CA148:92237 (2007).*
Ramakrishna et al. "Substituted indolyl . . . " CA150:329617 (2009).*
Sobri et al. "Radiosynthesis . . . " Bioorg. med. Chem. v.8, p. 2511-2518 (2000).*
Smith et al. "Solid phase synthesisi . . . " Bioorg. Med. Chem. Lett. v.10, p. 2693-2696 (2000).*
Wikipedia "Antipsychotic" p. 1-11 (2009).*
Awadallah "Synthesis pharmacophore . . . " Sci. Pharm. v.76, p. 415-438 (2008).*
Stiefl et al. "ErG:2D pharmacophore . . . " J. chem. Inf. Model. v.46 p. 208-220 (2006).*

* cited by examiner

*Primary Examiner*—Celia Chang
(74) *Attorney, Agent, or Firm*—Millen, White, Zelano & Branigan, P.C.

(57) ABSTRACT

Compounds of the formula (I), in which $R^1$, $R^2$, Q, X, Y, m and n have the meanings indicated in Claim (1), are potent $5\text{-HT}_{2A}$ antagonists and are suitable for the treatment of psychoses, schizophrenia, depression, neurological disorders, memory disorders, Parkinson's disease, amyotrophic lateral sclerosis, Alzheimer's disease, Huntington's disease, eating disorders, such as bulimia, anorexia nervosa, of premenstrual syndrome and/or for positively influencing obsessive-compulsive disorder (OCD).

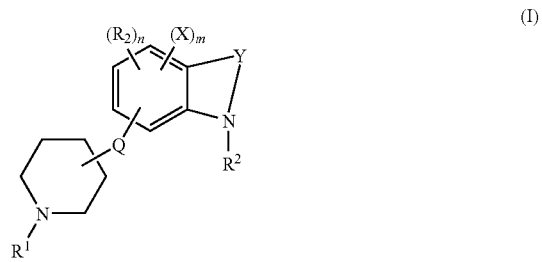

20 Claims, No Drawings

PIPERIDINE DERIVATIVES

The invention relates to compounds of the formula I

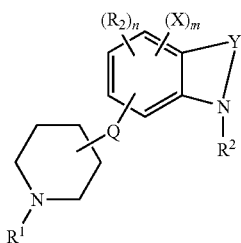

in which

X denotes H or F, Cl, Br, I, CN, OCN, SCN, $COR^2$, $COOR^2$, $CONR^2R^3$, imidazolyl, pyrazolyl, triazolyl or tetrazolyl, Y denotes —$CHR^2$—$CHR^2$— or —$CR^2$=$CR^2$—, Q denotes O, OH, NH, $NH^2$, $NR^2R^3$, C=O, CHOH, $CHNH_2$, C=NH, $CHOR^2$ or $CNR^2R^3$, $R^1$ denotes branched or unbranched alkylcycloalkyl, alkaryl or alkheteroaryl, each of which is mono- or polysubstituted by X, $R^2$ denotes H or linear or branched alkyl or alkaryl, $R^3$ denotes H or $R^2$, and m and n, independently of one another, denote 1, 2 or 3, and salts, solvates, racemates, enantiomers and diastereomers thereof and mixtures thereof in all ratios.

The invention was based on the object of finding novel compounds having valuable properties, in particular those which can be used for the preparation of medicaments.

It has been found that the compounds of the formula I and physiologically acceptable salts and solvates thereof, while being well tolerated, have valuable pharmacological properties since they have actions on the central nervous system. The compounds have strong affinity to 5-$HT_{2A}$ receptors, they furthermore exhibit 5-$HT_{2A}$ receptor-antagonistic properties.

For in-vitro detection of the affinity to 5-$HT_{2A}$ receptors, the following test (Example A1), for example, can be used. The 5-$HT_{2A}$ receptors are exposed both to [$^3$H]ketanserine (a substance known for its affinity to the receptor) and also to the test compound. The decrease in the affinity of [$^3$H]ketanserine to the receptor is an indication of the affinity of the test substance to the 5-$HT_{2A}$ receptor. The detection is carried out analogously to the description by J. E. Leysen et al., Molecular Pharmacology, 1982, 21: 301-314, or as also described, for example, in EP 0320983.

The efficacy of the compounds according to the invention as 5-$HT_{2A}$ receptor antagonists can be measured in vitro analogously to W. Feniuk et al., Mechanisms of 5-hydroxytryptamine-induced vasoconstriction, in: The Peripheral Actions of 5-Hydroxytryptamine, ed. Fozard J R, Oxford University Press, New York, 1989, p. 110. Thus, the contractility of the rat tail artery caused by 5-hydroxytryptamine is mediated by 5-$HT_{2A}$ receptors. For the test system, vessel rings prepared from the ventral rat tail artery are subjected to perfusion in an organ bath containing an oxygen-saturated solution. By introducing increasing concentrations of 5-hydroxytryptamine into the solution, a response is obtained to the cumulative concentration of 5-HT. The test compound is then added to the organ bath in suitable concentrations, and a second concentration curve for 5-HT is measured. The strength of the test compound in shifting the 5-HT-induced concentration curve to higher 5-HT concentrations is a measure of the 5-$HT_{2A}$ receptor-antagonistic property in vitro.

The 5-$HT^{2A}$-antagonistic property can be determined in vivo analogously to M. D. Serdar et al., Psychopharmacology, 1996, 128: 198-205.

Other compounds which likewise exhibit 5-$HT_2$-antagonistic actions are described, for example, in EP 0320983.

WO 99/11641 describes phenylindole derivatives having 5-$HT_2$-antagonistic properties.

The compounds of the formula I are therefore suitable both in veterinary and in human medicine for the treatment of functional disorders of the central nervous system and of inflammation. They can be used for the prophylaxis of and for combating the consequences of cerebral infarction phenomena (apoplexia cerebri), such as strokes and cerebral ischaemia, and for the treatment of extrapyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord traumas. In particular, however, they are suitable as medicament active ingredients for anxiolytics, antidepressants, antipsychotics, neuroleptics, antihypertonics and/or for positively influencing obsessive-compulsive disorder (OCD; for example WO 9524194), anxiety states and physiological changes associated with anxiety states, such as, for example, tachycardia, tremor or sweating (for example EP 319962), panic attacks, psychoses, schizophrenia, anorexia, delusional obsessions, agoraphobia, migraine, Alzheimer's disease, sleeping disorders, such as sleep apnoea, tardive dyskinesia, learning disorders, age-dependent memory disorders, eating disorders, such as bulimia, drugs misuse, such as, for example, of alcohol, opiates, nicotine, psychostimulants, such as, for example, cocaine or amphetamines (for example U.S. Pat. No. 6,004,980), sexual dysfunctions, conditions of pain of all types and fibromyalgia (for example WO 9946245).

The compounds of the formula I are suitable for the treatment of extrapyramidal side effects (EPS) in neuroleptic drug therapy. EPS is characterised by Parkinson's-like syndromes, acathisia and dystonic reactions (for example EP 337136). They are furthermore suitable for the treatment of anorexia nervosa, angina, Reynaud's phenomenon, coronary vasospasms, in the prophylaxis of migraine (for example EP 208235), pain and neuralgia (for example EP 320983), for the treatment of Reft syndrome with autistic traits, of Asperger's syndrome, of autism and autistic disorders, in concentration deficit states, developmental disorders, hyperactivity states with mental underdevelopment and stereotypical behaviour states (for example WO 9524194).

They are furthermore suitable for the treatment of endocrine diseases, such as hyperprolactinaemia, furthermore in vasospasms, thrombotic diseases (for example WO 9946245), hypertension and gastrointestinal diseases.

They are furthermore suitable for the treatment of cardiovascular diseases and extrapyramidal symptoms, as described in WO 99/11641 on page 2, line 24-30.

The compounds according to the invention are furthermore suitable for reducing the intraocular pressure and for the treatment of glaucoma.

They are also suitable for the prophylaxis and treatment of poisoning phenomena on administration of ergovaline to animals.

The compounds are furthermore suitable for the treatment of diseases of the cardiovascular system (WO 99/11641, page 3, line 14-15). The compounds according to the invention can also be employed together with other active ingredients in the treatment of schizophrenia. Suitable other active ingredients are the compounds mentioned in WO 99/11641 on page 13, line 20-26.

The compounds of the formula I according to the invention are preferably used for the treatment of diseases which are attributed to defective serotonergic transmission: as medicaments for anxiolytics (social and generalised anxiety disorders), Huntington's disease, tic disorders, schizotypical personality disorders, psychotic and cognitive symptoms in tardive dyskinesia, for the prevention of schizophrenia and treatment of cognitive deficits in first-degree relatives of schizophrenic patients, for the treatment of bipolar disorders, as adjuvant in low-dose typical neuroleptic therapy, for the treatment of therapy-resistant schizophrenia, the prodromal phase of schizophrenia, of atrioventricular conduction disturbances in children and youths, of attention deficit/hyperactivity disorder, substance misuse and dependence disorders and demented behaviour disorders, obsessive-compulsive disorders (OSD), as antidepressants, antipsychotics, antipsychotics in Parkinson's patients, against obesity and/or in insomnia, sleeping disorders of all types. Cardiovascular disorders, such as various angina diseases, Reynaud's syndrome, intermittent claudiaction, cardiac or peripheral vascular spasms, fibromyalgia, cardiac arrhythmia, thrombotic diseases.

They can furthermore be employed as intermediates for the preparation of further medicament active ingredients.

The invention relates to the compounds of the formula I and physiologically acceptable acid-addition salts thereof. The invention also relates to the solvates, for example hydrates or alcoholates, of these compounds.

The invention accordingly relates to the compounds of the formula I and to a process for the preparation of compounds of the formula I according to claim 1.

The invention also relates to the compounds of the formula I according to claim 1 and physiologically acceptable salts and solvates thereof as medicaments.

In particular, the invention relates to the compounds of the formula I according to claim 1 and physiologically acceptable salts and solvates thereof as medicaments having a 5-HT$_{2A}$ receptor-antagonistic action.

The invention also relates to the compounds of the formula I and enantiomers and diastereomers thereof and salts thereof.

For all radicals which occur more than once, their meanings are independent of one another.

The radical $R^2$ denotes alkyl or alkaryl and has 1 to 12, preferably 1, 2, 3, 4, 5, 6, 7 or 8, in particular 1 or 2, C atoms. Alkyl therefore denotes, in particular, for example, methyl, furthermore ethyl, n-propyl, isopropyl, n-butyl, sec-butyl or tert-butyl, furthermore also pentyl, 1-, 2- or 3-methyl-butyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethyl-butyl, 1-ethyl-1-methylpropyl, 1-ethyl-2-methylpropyl, 1,1,2- or 1,2,2-tri-methylpropyl, furthermore trifluoromethyl or pentafluoroethyl. Alkaryl preferably denotes alkylphenyl, in particular benzyl or phenethyl.

$R^1$ is preferably alkylcycloalky, in particular alkylcyclohexyl or alkylcyclopentyl, which is mono-X-substituted. Particular preference is given to cycloxylethyl or -methyl or cyclopentylethyl or -methyl. $R^1$ furthermore preferably denotes alkaryl or alkheteroaryl, in particular phenetyl, p-fluorophenethyl, 1-(1-methyl-2-phenylethyl)- or 2-(4-pyridyl) ethyl.

Q preferably denotes C=O, CHOH or CHNH$_2$.

X preferably denotes F, Cl, Br, CN, OCN, COR$^2$, COOR$^2$, CONH$_2$ or imdazolyl, in particular F, Cl, CN, COOR or CONH$_2$.

Y is preferably -CH$_2$—CH(R$^2$)— or —CH=CR$^2$—, in particular —CH$_2$CH$_2$—, —CH=CH—, —CH$_2$—CH(CN)—, —CH=C(CN)—, —CH$_2$—CH(COCF$_3$)— or —CH=C(COCF$_3$)—.

The group defined by Y is preferably linked to N at the unsubstituted C atom and to the aromatic ring at the substituted C atom.

m and n preferably denote 1.

The piperidinyl group in the compounds of the formula I is preferably bonded to the group Q the 3- or 4-position, in particular via the 4-position.

Accordingly, the invention relates, in particular, to the compounds of the formula I in which at least one of the said radicals has one of the preferred meanings indicated above.

Preferred sub-formulae of the formula I are formulae IA and IB:

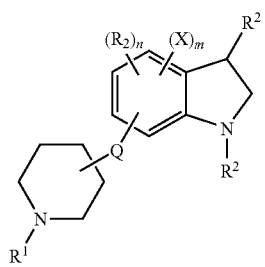

IA

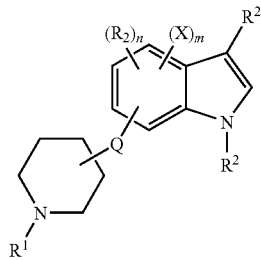

IB

Particular preference is given to the following compounds I1 to I7 according to the invention:

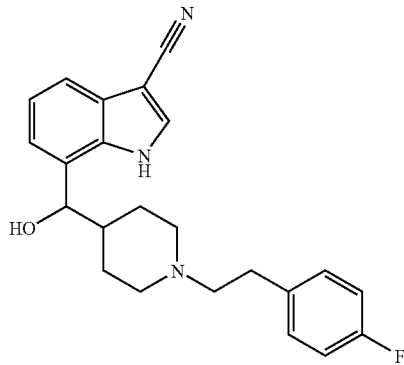

I1

-continued

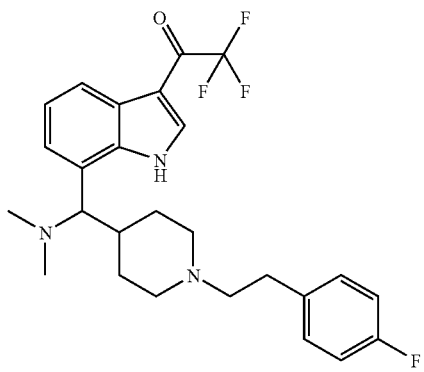
I2

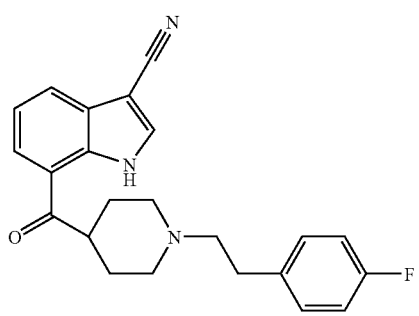
I3

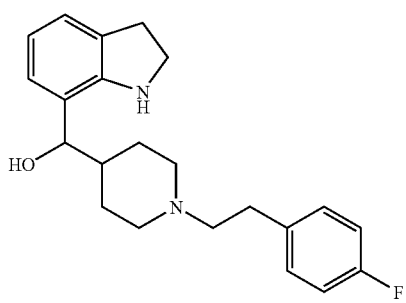
I4

I5

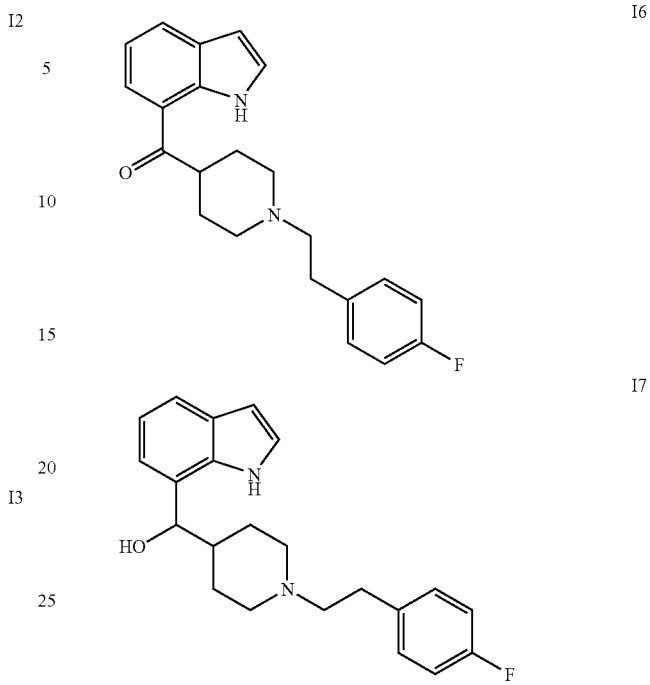

And salts, solvates, racemates, enantiomers and diastereomers thereof and mixtures thereof in all ratios.

The compounds of the formula I7 is particularly preferred.

The compounds of the formula I and also the starting materials for their preparation are, in addition, prepared by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York;), to be precise under reaction conditions as are known and suitable for the said reactions. Use can also be made here of variants known per se which are not mentioned in greater detail here.

If desired, the starting materials for the claimed process can also be formed in situ in such a way that they are not isolated from the reaction mixture, but instead are immediately converted further into the compounds of the formula I. On the other hand, it is possible to carry out the reaction stepwise.

If desired, the free bases of the formula I can be liberated from their salts by treatment with strong bases, such as sodium hydroxide, potassium hydroxide, sodium carbonate or potassium carbonate, if no further acidic groups are present in the molecule. In those cases where the compounds of the formula I have free acid groups, salt formation can likewise be achieved by treatment with bases. Suitable bases are alkali metal hydroxides, alkaline-earth metal hydroxides or organic bases in the form of primary, secondary or tertiary amines.

The invention furthermore relates to the medicaments according to the invention having a 5-HT$_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders, such as bulimia, anorexia nervosa, of premenstrual syndrome and/or for positively influencing obsessive-compulsive disorder (OCD).

The invention also relates to a pharmaceutical composition comprising at least one medicament according to the invention and optionally excipients and/or adjuvants and optionally other active ingredients.

The medicaments here can be brought into a suitable dosage form together with at least one solid, liquid and/or semi-liquid excipient or adjuvant and optionally in combination with one or more further active ingredient(s).

The invention furthermore relates to the use of the compounds according to the invention and/or of physiologically acceptable salts and solvates thereof for the preparation of a medicament having a 5-$HT_{2A}$ receptorantagonistic action.

The invention also relates to the use of the compounds according to the invention and/or of physiologically acceptable salts and solvates thereof for the preparation of a medicament having a 5-$HT_{2A}$ receptor-antagonistic action for the treatment of psychoses, schizophrenia, depression, neurological disorders, memory disorders, Parkinson's disease, amyotrophic lateral sclerosis, Alzheimer's disease, Huntington's disease, eating disorders, such as bulimia, anorexia nervosa, of premenstrual syndrome and/or for positively influencing obsessive-compulsive disorder (OCD).

The pharmaceutical compositions can be employed as medicaments in human and veterinary medicine. Suitable excipient substances are organic or inorganic substances which are suitable for enteral (for example oral), parenteral or topical administration and do not react with the novel compounds, for example water, vegetable oils, benzyl alcohols, polyethylene glycols, gelatine, carbohydrates, such as lactose or starch, magnesium stearate, talc, Vaseline. Suitable for enteral administration are, in particular, tablets, dragees, capsules, syrups, juices, drops or suppositories, suitable for parenteral administration are solutions, preferably oily or aqueous solutions, furthermore suspensions, emulsions or implants, suitable for topical use are ointments, creams or powders. The novel compounds may also be lyophilised and the resultant lyophilisates used, for example, for the preparation of injection preparations.

The compositions indicated may be sterilised and/or comprise adjuvants, such as lubricants, preservatives, stabilisers and/or wetting agents, emulsifiers, salts for modifying the osmotic pressure, buffer substances, dyes, flavours and/or aromas. If desired, they may also comprise one or more further active ingredients, for example one or more vitamins.

The substances according to the invention are generally administered here analogously to known preparations, preferably in doses between about 0.1 and 500 mg, in particular between 5 and 300 mg, per dosage unit. The daily dose is preferably between about 0.01 and 250 mg/kg, in particular between 0.02 and 100 mg/kg, of body weight.

The substances according to the invention are generally preferably administered here in doses between about 1 and 500 mg, in particular between 5 and 100 mg, per dosage unit. The daily dose is preferably between about 0.02 and 10 mg/kg of body weight. However, the specific dose for each particular patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

Above and below, all temperatures are indicated in ° C. In the examples below, "conventional work-up" means: if necessary, the solvent is removed, if necessary, water is added, if necessary, depending on the constitution of the end product, pH values of between 2 and 10 are set, the mixture is extracted with ethyl acetate or dichloromethane, the phases are separated, the organic phase is dried over sodium sulfate, filtered and evaporated, and the product is purified by chromatography on silica gel and/or by crystallisation.

EXAMPLE 1

Synthesis of 1-{1-[2-(4-fluorophenyl)ethyl]piperidin-4-yl}-1-(1H-indol-7-yl)-methanol

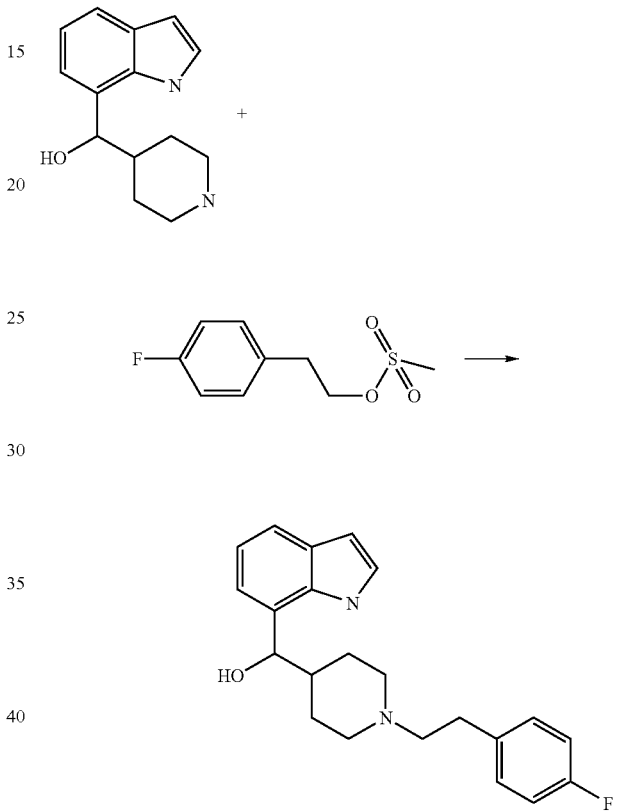

500 mg (2 mmol) of (1H-indol-7-yl)piperidin-4-ylmethanol and 400 mg (2 mmol) of 2-(4-fluorophenyl)ethyl methanesulfonate were dissolved in 50 ml of acetonitrile with 0.7 ml of N-ethyldiisopropylamine, and the mixture is warmed at 80° C. for 12 h. After cooling, the solvent was removed under reduced pressure, and the residue was partitioned between ethyl acetate and water. After neutralisation using 1 N NaOH, the organic phase was separated off, dried over $Na_2SO_4$ and, after evaporation, purified by chromatography.

TLC: ethyl acetate/methanol 8:2 $R_F$: 0.2

Melting point: 198.0-199.0° C.

500 MHz 1H-NMR (DMSO-d6) δ 10.74 (br. s, 1H); 7.39 (d, 1H, J=7.6 Hz); 7.26 (t, 1H, J=2.6 Hz); 7.22 (m, 2H); 7.06 (m, 2H), 6.99 (m, 1H); 6.94 (t, 1H, J=7.6 Hz); 6.99 (m, 1H); 6.94 (t, 1H, J=7.6 Hz); 6.39 (dd, 1H, J=3.1 Hz, J=1.9 Hz); 5.23 (d, 1H, J=4.0 Hz); 4.69 (dd, 1H, J=7.0 Hz, J=4.0 Hz); 2.96 (br. d, 1H, J=9.3 Hz); 2.68 (br. t, 2H, J=7.2 Hz); 2.44 (br. s, 2H); 1.85 (m, 2H); 1.77 (br. s, 1H); 1.37-1.26 (m, 2H); 1.17 (m, 2H)

[M+H$^+$]=353

EXAMPLE 2

Synthesis of 1-{1-[2-(4-fluorophenyl)ethyl]piperidin-4-yl}-1-(1H-indol-7-yl)-methanones

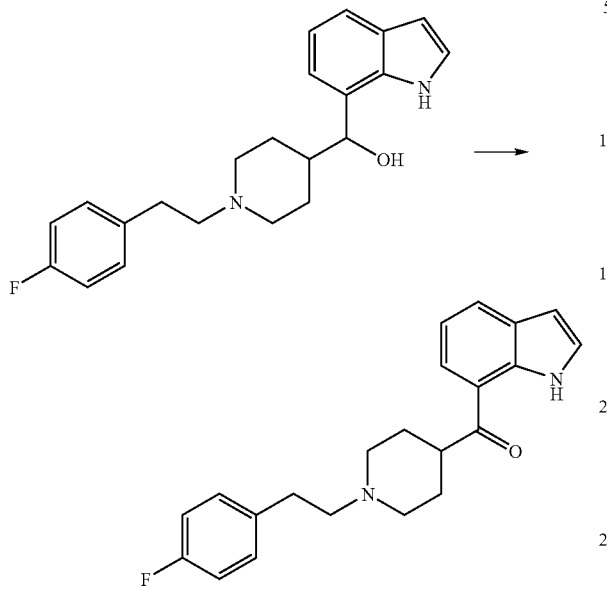

500 mg (1.4 mmol) of 1-{1-[2-(4-fluorophenyl)ethyl]piperidin-4-yl}-1-(1H -indol-7-yl)methanol were dissolved in 20 ml of dichloromethane, and 5.3 ml of a 15% solution of 1,1,1-triacetoxy-1,1dihydro-1,2-benziodoxol-3(1H)-one in dichloromethane were added dropwise at 0° C. The batch was allowed to warm from 0° C. to RT over the course of 3 h, and the suspension was then added to 20 ml of water. After being rendered alkaline using 1 N NaOH, the phases were separated, the organic phase was dried over $Na_2SO_4$ and, after evaporation, was purified by chromatography.

TLC: ethyl acetate/methanol 8:2 $R_F$: 0.4

Melting point: 132.0-133.0° C.

400 MHz $^1$H-NMR (DMSO-d6) δ 11.44 (br. s, 1H); 7.93 (d, 1H, J=8.2 Hz); 7.88 (d, 1H, J=7.9 Hz); 7.39-7.10 (m, 6H); 6.55 (dd, 1H, J=1.9 Hz; J=3.1 Hz); 3.53 (m, 1H); 3.01 (m, 2H); 2.74 (m, 2H); 2.54 (m, 2H); 2.17 (m, 2H); 1.84-1.61 (m, 4H).

235 MHz $^{19}$F NMR (DMSO-d6)-116.29 ppm

[M+H$^+$]=352

EXAMPLE 3

Synthesis of 7-(1-{1-[2-(4-fluorophenyl)ethyl]piperidin-4-yl}methanoyl)-1H-indole-3-carbonitriles hydrochloride

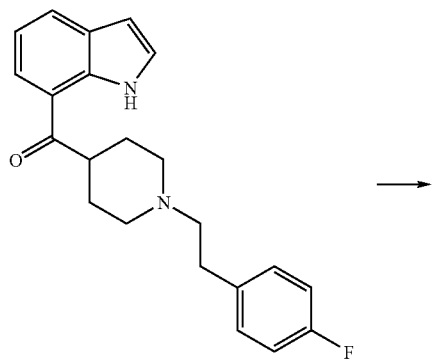

650 mg (4.2 mmol) of phosphoryl chloride were added dropwise to 10 ml of DMF with ice cooling at 20-30° C. A solution of 1.2 g (3.4 mmol) of 1-{1-[2-(4-fluorophenyl)ethyl]piperidin-4-yl}-1-(1H-indol-7-yl)methanone in 10 ml of DMF was subsequently added dropwise at RT, during which the temperature rose to 60° C. The mixture was stirred at 125° C. for 1 h. A warm solution of 0.5 g (7.2 mmol) of hydroxylammonium chloride in 5 ml of DMF was subsequently added dropwise, and the mixture was stirred at 120° C. for a further 15 minutes. The reaction mixture was subsequently cooled to RT and added to ice-water. The mixture was extracted with ethyl acetate, the organic phase was dried over $Na_2SO_4$, evaporated and purified by chromatography. After removal of the eluent under reduced pressure, the product fractions were dissolved in acetone, adjusted to pH=3 using ethanolic hydrochloric acid, and the white crystals depositing were filtered off with suction, washed with ether and dried in air.

TLC: ethyl acetate/methanol 8:2 $R_F$:0.5

Melting point: 274-276° C.

[M+H$^+$]=376

500 MHz $^1$H-NMR (DMSO-d6) δ 12.39 (br. d, 1H, J=2.4 Hz); 10.84 (br. s, 1H); 8.26 (d, 1H, J=3.1 Hz); 8.20 (d, 1H, J=7.7 Hz); 8.02 (d, 1H, J=7.7 Hz); 7.45 (t, 1H, J=7.7 Hz); 7.36 (m, 2H); 7.19 (m, 2H); 3.91 (m, 1H); 3.66 (br. d, 2H, J=11.8 Hz); 3.29 (m, 2H); 3.13 (m, 4H); 2.10 (m, 4H).

EA ($C_{23}H_{22}FN_3O$—HCl) calc. C, 67.1%, H, 5.6%, N, 10.2% found C, 66.4%, H, 5.7%, N, 10.3%

EXAMPLE 4

Synthesis of 1-(2,3-dihydro-1H-indol-7-yl)-1-{1-[2-(4-fluorophenyl)ethyl]-piperidin4-yl}methanol

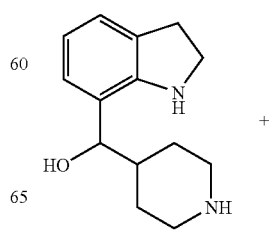

+

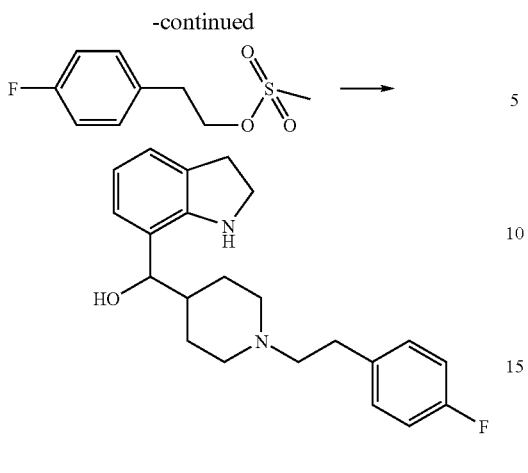

→

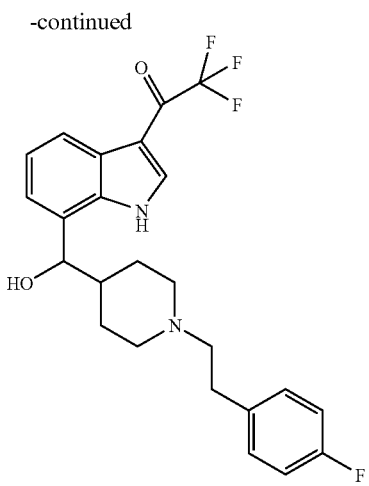

900 mg (4 mmol) of (2,3-dihydro-1H-indol-7yl)piperidin4-ylmethanol, 850 mg (4 mmol) of 2-(4-fluorophenyl)ethyl methanesulfonate were dissolved in 50 ml of acetonitrile with 2 ml of N-ethyldiisopropylamine, and the mixture was warmed at 80° C. for 12 h. After cooling, the solvent was removed under reduced pressure, and the residue was partitioned between ethyl acetate and water. After neutralisation using 1N NaOH, the organic phase was separated off, dried over $Na_2SO_4$ and, after evaporation, purified by chromatography.

TLC: ethyl acetate/methanol 8:2 $R_F$:0.2

Melting point: 151.5-153.0° C.

400 MHz 1H-NMR (DMSO-d6) δ 7.23 (m, 2H); 7.07 (m, 2H); 6.91 (d, 1H, J=7.7 Hz); 6.84 (d, 1H, J=7.7 Hz); 6.50 (t, 1H, J=7.4 Hz); 5.13 (s, 1H); 4.99 (d, 1H 3.49 Hz); 4.26 (dd,$_1$H, J=3.32 Hz; J=6.33 Hz); 3.41 (m, 1H); 2.95 (br. d, 1H, J=10.00 Hz); 2.88 (m, 3H); 2.69 (m, 2H); 2.46 (m, 2H); 1.81 (m, 3H); 1.55 (br. s, 1H); 1.26 (m, 3H).

[M+H$^+$]=355

EXAMPLE 5

Synthesis of 2,2,2-trifluoro-1-[7-({1-[2-(4-fluorophenyl)ethyl]piperidin-4-yl}-hydroxymethyl)-1H-indol-3-yl]ethanone 1 g (3 mmol) of {1-[2-(4-fluorophenyl)ethyl]piperidin-4-yl}-(1H-indol-7-yl)-methanol were dissolved in 10 ml of THF with 20 ml of trifluoroacetic anhydride. The mixture was stirred at RT for 3 h, and the solvent was subsequently removed under reduced pressure. 1.3 g of a brown oil were isolated.

TLC: ethyl acetate/methanol 8:2 $R_F$:0.2

300 MHz $^1$H-NMR (DMSO-d6) δ 12.34 (br. s, 1H); 8.27 (d, 1H, J=1.9 Hz); 8.09 (dd, 1H, J=1.6 Hz, J=7.4 Hz); 7.30-7.20 (m, 4H); 7.10-7.02 (m, 2H); 5.58 (br. s, 1H); 4.78 (d, 1H, J=6.9 Hz); 3.32 (br. s, 1H); 2.95 (m, 1H); 2.83 (m, 1H); 2.67 (m, 2H); 2.43 (m, 2H); 1.82 (m, 2H); 1.62 (m, 1H); 1.33 (m, 2H); 1.19 (m, 1H).

75 MHz 13C-NMR (DMSO-d6) d 173.92 (C=O); 158.97 (C—F); 137.00; 136.66; 134.16; 130.26; 130.16; 129.92; 126.11; 123.12; 122.25; 119.48; 114.85; 114.58; 108.61 (C-aromatic); 118.81 (CF$_3$); 73.96 (C—OH); 59.79; 53.21; 53.09 (C$_3$—N); 42.88; 31.89; 28.09; 27.91 (C-alkyl).

235 MHz $^{19}$F-NMR (DMSO-d6) δ −114.45; −63.19

EXAMPLE 6

Synthesis of 1-[7-(dimethylamino-{1-[2-(4-fluorophenyl)ethyl]piperidin-4-yl}-methyl)-1H-indol-3-yl]-2,2,2-triflouroethanone

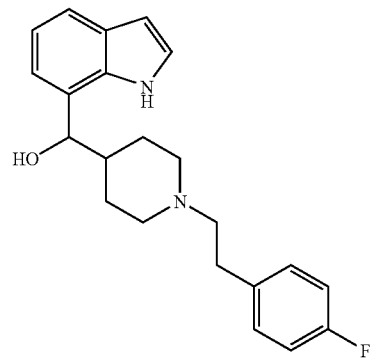

→

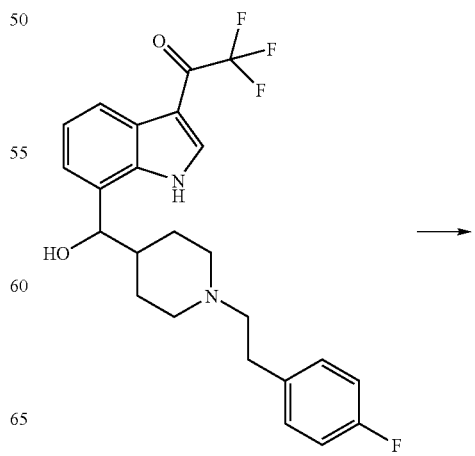

→

-continued

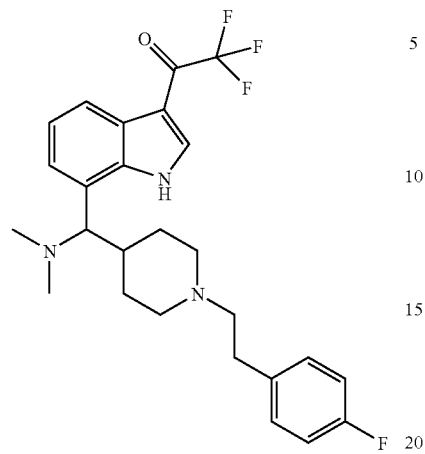

550 mg (3.6 mmol) of phosphoryl chloride were added dropwise to 10 ml of DMF with ice cooling at 20-30° C. A solution of 1.3 g (2.9 mmol) of 2,2,2-trifluoro-1-[7-({1-[2-(4-fluorophenyl)ethyl]piperidin-4-yl}hydroxymethyl)-1H-indol-3-yl]ethanone in 10 ml of DMF was subsequently added dropwise at RT, during which the temp. rose to 60° C. The mixture was left to stir at 125° C. for a further 1 h, and a warm solution of 0.5 g (6.5 mmol) of hydroxylammonium chloride in 5 ml of DMF was then added. The mixture was stirred at 120° C. for a further 15 min.

After the reaction mixture had cooled to RT, it was poured into ice-water, rendered alkaline using NaOH and subsequently extracted with ethyl acetate. The organic phase was dried over $Na_2SO_4$ and evaporated. The product was purified by chromatography.

TLC: ethyl acetate/methanol 8:2 $R_F$:0.1

250 MHz $^1$H-NMR (DMSO-d6) δ 12.52 (br. s, 1H); 8.33 (d, 1H, J=1.9 Hz); 8.12 (dd, 1H, J=1.0 Hz, J=7.9 Hz); 7.33 8t, 1H, J=7.6 Hz); 7.19 (m, 3H); 7.08-7.01 (m, 2H); 3.79 (d, 1H, J=7.8 Hz); 3.31 (br. s, 1H); 2.90 (m, 1H); 2.85 (m, 1H); 2.66 (m, 2H); 2.43 (m, 2H); 1.80 (m, 2H); 1.59 (m, 1H); 1.30 (m, 2H); 1.20 (m, 1H).

235 MHz $^{19}$F-NMR (DMSO-d6) δ−116.75; −72.70

The products can be used as therapeutic agents, diagnostic agents or as reagents. They can be given to humans or animals locally or systemically, orally, intravenously, intraperitoneally, intramuscularly, subcutaneously, transdermally, nasally, buccally or iontophoretically, which includes formulations in suspensions, emulsions or solutions, liposomes, ointments, pastes, biodegradable polymers or as nanoparticles, tablets, capsules or pills, granules or powders, as aerosol for inhalation, as intranasal drops or sprays, where further formulations are also conceivable.

The following compounds according to the invention are obtained analogously using the corresponding precursors:

EXAMPLES 7-17

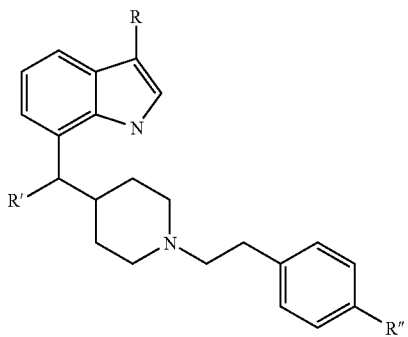

|    | R      | R'         | R''  |
|----|--------|------------|------|
| 7  | F      | OH         | F    |
| 8  | F      | $NH_2$     | F    |
| 9  | OCN    | OH         | F    |
| 10 | OCN    | $N(CH_3)_2$ | F   |
| 11 | F      | OH         | CN   |
| 12 | F      | $NH_2$     | CN   |
| 13 | OCN    | OH         | CN   |
| 14 | OCN    | $N(CH_3)_2$ | CN  |
| 15 | $COCF_3$ | OH       | CN   |
| 16 | $COCF_3$ | $NH_2$   | CN   |
| 17 | $COCF_3$ | $N(CH_3)_2$ | CN |

EXAMPLES 18-28

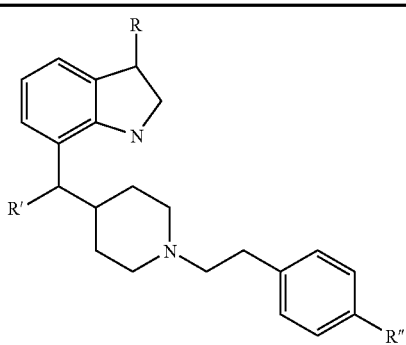

|    | R      | R'         | R''  |
|----|--------|------------|------|
| 18 | F      | OH         | F    |
| 19 | F      | $NH_2$     | F    |
| 20 | OCN    | OH         | F    |
| 21 | OCN    | $N(CH_3)_2$ | F   |
| 22 | F      | OH         | CN   |
| 23 | F      | $NH_2$     | CN   |
| 24 | OCN    | OH         | CN   |
| 25 | OCN    | $N(CH_3)_2$ | CN  |
| 26 | $COCF_3$ | OH       | CN   |
| 27 | $COCF_3$ | $NH_2$   | CN   |
| 28 | $COCF_3$ | $N(CH_3)_2$ | CN |

The following examples relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $NaH_2PO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is transferred into ampoules, lyophilised under aseptic conditions and sealed under sterile conditions. Each ampoule contains 10 mg of active ingredient.

The invention claimed is:

1. A compound of formula I

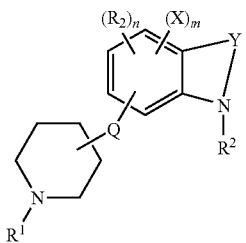

in which
X denotes H, F, Cl, Br, I, CN, OCN, SCN, $COR^2$, $COOR^2$, $CONR^2R^3$, imidazolyl, pyrazolyl, triazolyl or tetrazolyl,
Y denotes —$CHR^2$—$CHR^2$— or —$CR^2$=$CR^2$—,
Q denotes, C=O, CHOH, $CHNH_2$, C=NH, $CHOR^2$ or $CNR^2R^3$,
$R^1$ denotes branched or unbranched alkylcycloalkyl, alkaryl or alkheteroaryl, each of which is mono- or polysubstituted by X,
$R^2$ denotes H or linear or branched alkyl or alkaryl,
$R^3$ denotes H or linear or branched alkyl or alkaryl, and
m and n, independently of one another, denote 1, 2 or 3,
or a salt, racemate, enantiomer or diastereomer thereof or a mixture thereof.

2. A compound according to claim 1, wherein
X denotes H, F or CN,
Y denotes —$CHR^2$—$CHR^2$— or —$CR^2$=$CR^2$—,
Q denotes C=O, CHOH, or $CNR^2R^3$,
$R^1$ denotes unbranched alkaryl, which is monosubstituted by X,
$R^2$ denotes H or linear alkyl, and
$R^3$ denotes H or linear alkyl.

3. A compound according to claim 1, wherein
X denotes H or F,
Y denotes —$CHR^2$—$CHR^2$— or —$CR^2$=$CR^2$—,
Q denotes C=O, CHOH, or $CNR^2R^3$,
$R^1$ denotes unbranched alkaryl, which is monosubstituted by X,
$R^2$ denotes H or linear alkyl, and
$R^3$ denotes H or linear alkyl.

4. A compound according to claim 1, wherein
X denotes H or F, or CN,
Y denotes —$CR^2$=$CR^2$—,
Q denotes CHOH,
$R^1$ denotes unbranched alkaryl, which is monosubstituted by X, wherein aryl is phenyl, and
$R^2$ denotes H.

5. A compound according to claim 1, wherein
X denotes H or F,
Y denotes —$CR^2$=$CR^2$—,
Q denotes CHOH,
$R^1$ denotes unbranched alkaryl, which is monosubstituted by X, wherein aryl is phenyl, and
$R^2$ denotes H.

6. A compound, which is of formula I1, I2, I3, I4, I5, I6 or I7
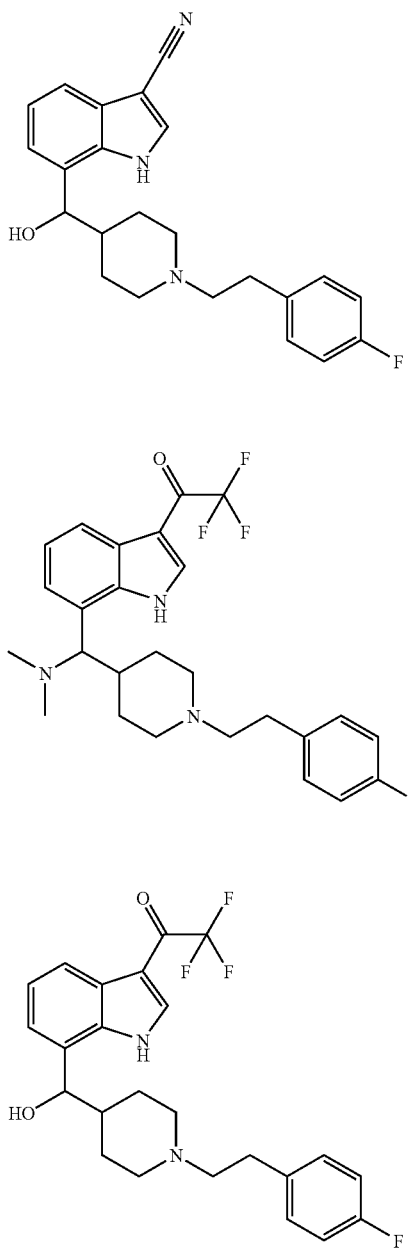
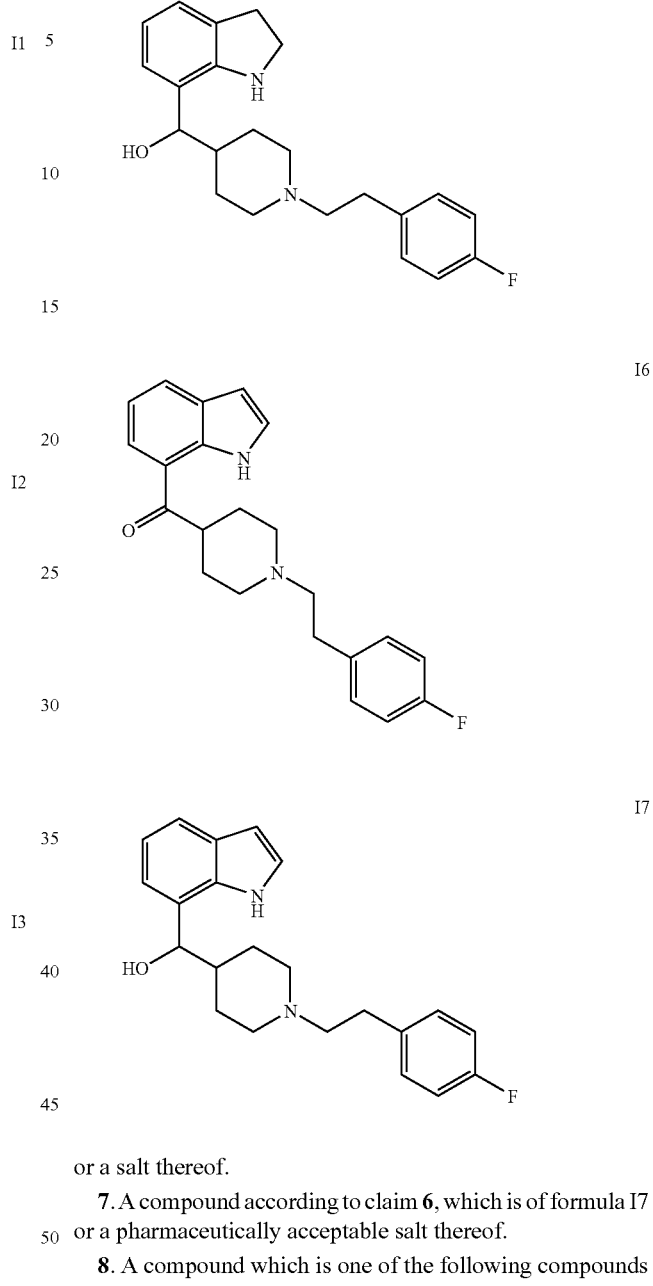
or a salt thereof.
7. A compound according to claim 6, which is of formula I7 or a pharmaceutically acceptable salt thereof.
8. A compound which is one of the following compounds
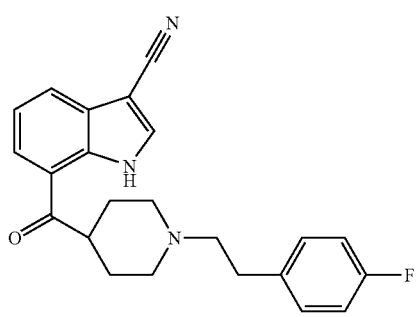
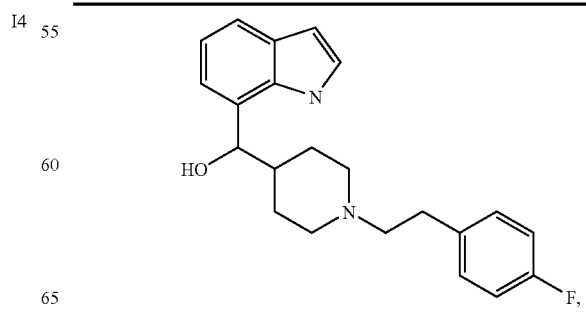

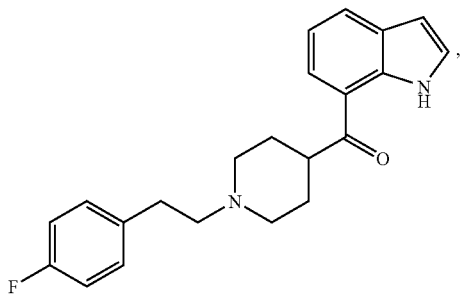
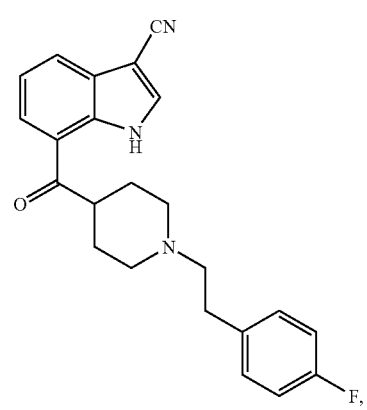
ClH
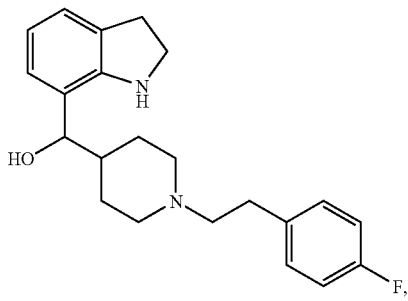
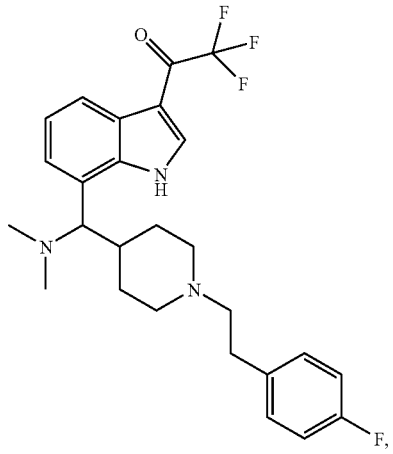
or
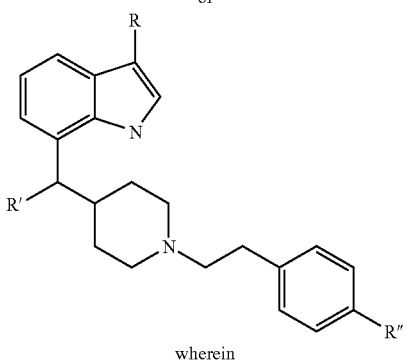
wherein
| R | R' | R" |
|---|---|---|
| F | OH | F |
| F | NH$_2$ | F |
| OCN | OH | F |
| OCN | N(CH$_3$)$_2$ | F |
| F | OH | CN |
| F | NH$_2$ | CN |
| OCN | OH | CN |
| OCN | N(CH$_3$)$_2$ | CN |
| COCF$_3$ | OH | CN |
| COCF$_3$ | NH$_2$ | CN or |
| COCF$_3$ | N(CH$_3$)$_2$ | CN |
or
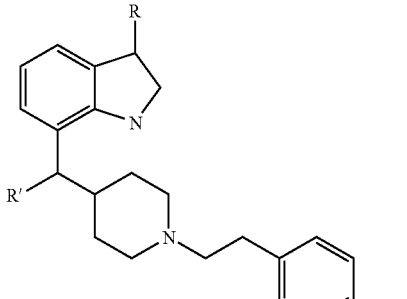
wherein
| R | R' | R" |
|---|---|---|
| F | OH | F |
| F | NH$_2$ | F |
| OCN | OH | F |
| OCN | N(CH$_3$)$_2$ | F |
| F | OH | CN |

-continued

| | | |
|---|---|---|
| F | NH$_2$ | CN |
| OCN | OH | CN |
| OCN | N(CH$_3$)$_2$ | CN |
| COCF$_3$ | OH | CN |
| COCF$_3$ | NH$_2$ | CN or |
| COCF$_3$ | N(CH$_3$)$_2$ | CN | or a salt thereof.

9. A pharmaceutical composition, comprising a compound of claim 1 and a pharmaceutically acceptable carrier.

10. A method for antagonizing a 5-HT$_{2A}$ receptor, comprising administering to a subject in need thereof an effective amount of a compound of claim 1.

11. A method for treating psychoses, schizophrenia, depression, Parkinson's disease, amyotrophic lateral sclerosis, Alzheimer's disease, Huntington's disease, bulimia, a panic attack, anorexia nervosa, sleep apnoea, premenstrual syndrome, or obsessive-compulsive disorder (OCD), comprising administering to a subject in need thereof an effective amount of a compound of claim 1.

12. A pharmaceutical composition, comprising a compound of claim 6 and a pharmaceutically acceptable carrier.

13. A method for antagonizing a 5-HT$_{2A}$ receptor, comprising administering to a subject in need thereof an effective amount of a compound of claim 6.

14. A method for treating psychoses, schizophrenia, depression, Parkinson's disease, amyotrophic lateral sclerosis, Alzheimer's disease, Huntington's disease, bulimia, a panic attack, anorexia nervosa, sleep apnoea, premenstrual syndrome, or obsessive-compulsive disorder (OCD), comprising administering to a subject in need thereof an effective amount of a compound of claim 6.

15. A method for treating psychoses, comprising administering to a subject in need thereof an effective amount of a compound of claim 1.

16. A method for treating psychoses, comprising administering to a subject in need thereof an effective amount of a compound of claim 6.

17. A method for treating Parkinson's disease, comprising administering to a subject in need thereof an effective amount of a compound of claim 1.

18. A method for treating Parkinson's disease, comprising administering to a subject in need thereof an effective amount of a compound of claim 6.

19. A method for treating psychoses, comprising administering to a subject in need thereof an effective amount of a compound of claim 8.

20. A method for treating Parkinson's disease, comprising administering to a subject in need thereof an effective amount of a compound of claim 8.

* * * * *